United States Patent [19]

Rajani et al.

[11] Patent Number: 5,326,385
[45] Date of Patent: Jul. 5, 1994

[54] METHOD OF TREATING SOUR LIQUEFIED PETROLEUM GAS

[75] Inventors: Jayantilal B. Rajani; Thijme Last, both of Amsterdam; Michel Guirguis, Pernis; Johannes L. W. C. Den Boestert; Hendrik C. Rijkens, both of Amsterdam, all of Netherlands

[73] Assignee: Shell Oil Company, Houston, Tex.

[21] Appl. No.: 21,818

[22] Filed: Feb. 24, 1993

[30] Foreign Application Priority Data

Feb. 24, 1992 [EP] European Pat. Off. ............ 92200532

[51] Int. Cl.$^5$ .................... B01D 19/00; B01D 53/22
[52] U.S. Cl. ............................................ 95/46; 95/50;
208/209; 208/240; 423/228; 585/818
[58] Field of Search ...................... 95/43, 46, 50;
159/DIG. 27; 203/39; 208/179, 180, 208 R,
209, 237, 240, 251 R, 322; 423/228, 229, 563;
585/818, 819

[56] References Cited

U.S. PATENT DOCUMENTS

| | | | |
|---|---|---|---|
| 3,440,264 | 4/1969 | McVannel | 208/308 X |
| 3,919,075 | 11/1975 | Parc et al. | 208/180 |
| 3,990,963 | 11/1976 | Audibert et al. | 208/179 |
| 4,248,695 | 2/1981 | Swanson | 208/208 R X |
| 4,405,409 | 9/1983 | Tusel et al. | 203/39 X |
| 4,750,990 | 6/1988 | Kulkarni et al. | 208/251 R |
| 4,774,365 | 9/1988 | Chen et al. | 585/818 X |
| 4,857,078 | 8/1989 | Watler | 55/16 |
| 4,978,430 | 12/1990 | Nakagawa et al. | 203/39 X |
| 5,057,641 | 10/1991 | Valus et al. | 208/308 X |
| 5,095,170 | 3/1992 | Chen et al. | 208/308 X |
| 5,120,900 | 6/1992 | Chen et al. | 208/308 X |
| 5,133,851 | 7/1992 | Bitter et al. | 208/251 R |

FOREIGN PATENT DOCUMENTS

| | | |
|---|---|---|
| 1107659 | 8/1981 | Canada . |
| 0247585A1 | 12/1987 | European Pat. Off. . |
| 51038303 | 3/1976 | Japan . |
| 53144471 | 12/1978 | Japan . |
| 1237238 | 6/1986 | U.S.S.R. . |
| 2099446A | 12/1982 | United Kingdom . |
| WO92/10448 | 6/1992 | World Int. Prop. O. . |

OTHER PUBLICATIONS

Search Report dated Sep. 14, 1992 attached.

*Primary Examiner*—Robert Spitzer

[57] ABSTRACT

A method of treating sour liquefied petroleum gas comprising removing hydrogen sulfide from the sour liquefied petroleum gas by:

(a) contacting the liquefied petroleum gas in an extraction column with a liquid and regenerable absorbent to obtain purified liquefied petroleum gas;

(b) supplying the purified liquefied petroleum gas to a membrane unit comprising a membrane selected from a permselective membrane and a porous hydrophobic membrane, a permeate outlet and a retentate outlet; and (c) removing from the permeate outlet of the membrane unit treated liquefied petroleum gas and from the retentate outlet of the membrane unit contaminated liquefied petroleum gas.

25 Claims, 2 Drawing Sheets

METHOD OF TREATING SOUR LIQUEFIED PETROLEUM GAS

BACKGROUND OF THE INVENTION

1. Field of the Invention

The present invention relates to a method of removing hydrogen sulfide from sour liquefied petroleum gas.

2. Description of the Prior Art

Liquefied petroleum gas mainly consists of a mixture of propane, normal-butane and iso-butane. As used herein, the term "butane" refers to normal-butane, iso-butane and mixtures of normal-butane and iso-butane. Sour liquefied petroleum gas is liquefied petroleum gas which contains hydrogen sulfide. Sweet liquefied petroleum gas is liquefied petroleum gas which is relatively free of hydrogen sulfide.

Gaseous streams containing butane and lighter hydrocarbons are obtained in a refinery as gaseous overhead, for example, from a crude distillation column, or from fractionating a hydrocarbon-containing stream obtained by converting a heavy hydrocarbon-containing feed. Such a conversion method can be catalytic cracking or hydrotreating.

There are several methods to obtain a liquefied stream from the gaseous overhead. The gaseous stream can be compressed to a pressure from 10 bar to 30 bar (gauge) or it can be mixed with gasoline. Still additional methods involve chilling the gaseous stream or absorbing it in lean oil.

Liquefied petroleum gas is also obtained as by-product from the production of natural gas or hydrocarbon oil from an underground formation.

The present invention is directed to the removal of hydrogen sulfide from sour liquefied petroleum gas. Hydrogen sulfide is normally removed from sour liquefied petroleum gas by contacting the sour liquefied petroleum gas in an extraction column with a liquid and regenerable absorbent. Suitable absorbents include aqueous solutions of di-isopropanol amine or diethanol amine. An example of such a process is described in European Patent Application Publication No. 21 479.

The liquefied petroleum gas obtained after the removal of hydrogen sulfide contains contaminants such as absorbent, water and iron compounds. Although the liquefied petroleum gas containing contaminants can be used at the refinery, the contaminants need to be removed.

The present invention provides a method of removing hydrogen sulfide from sour liquefied petroleum gas which yields a stream of sweet liquefied petroleum gas that is substantially free of contaminants.

SUMMARY OF THE INVENTION

The present invention is directed to a method of removing hydrogen sulfide from sour liquefied petroleum gas which comprises:

(a) contacting the sour liquefied petroleum gas in an extraction column with a liquid and regenerable absorbent to obtain a sweet liquefied petroleum gas which contains contaminants;

(b) supplying the sweet liquefied petroleum gas which contains contaminants to a membrane unit comprising a membrane selected from a permselective membrane and a porous hydrophobic membrane, a permeate outlet and a retentate outlet; and (c) removing from the permeate outlet of the membrane unit a sweet liquefied petroleum gas stream which is substantially free of contaminants and from the retentate outlet of the membrane unit a sweet liquefied petroleum gas stream which contains concentrated contaminants.

DESCRIPTION OF THE PREFERRED EMBODIMENTS

Figure 1:
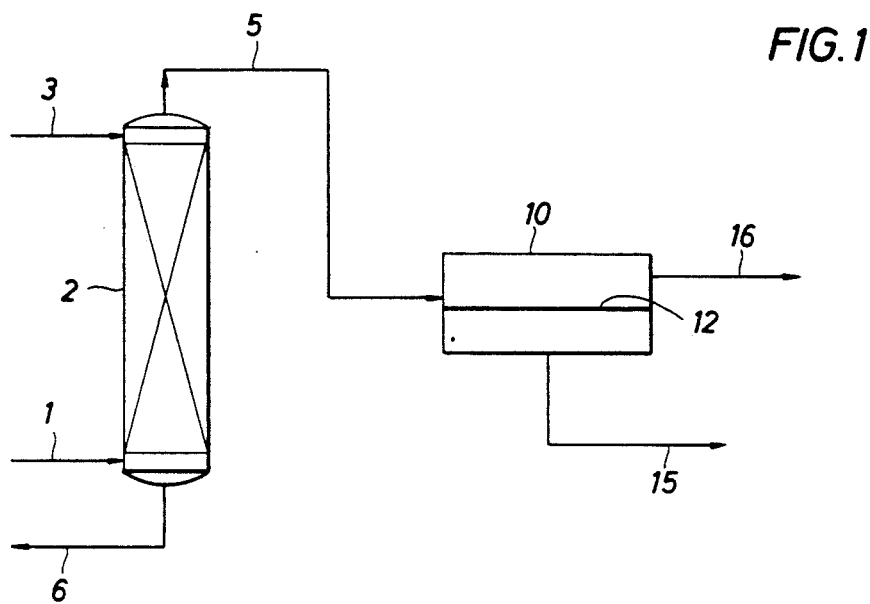
FIG. 1 is a schematic drawing of equipment for carrying out the invention.

The present invention provides a simple method for removing hydrogen sulfide from sour liquefied petroleum gas to obtain a sweet contaminated liquefied petroleum gas stream which can be used as fuel in the refinery and a sweet liquefied petroleum gas stream which is substantially free of contaminants, i.e., which contains less than about 10 parts per million contaminants. The contaminants remain in the liquefied petroleum gas stream which is removed from the retentate outlet of the membrane unit so that fouling of the membrane is avoided. The flow of the retentate permanently cleans the membrane.

In the present invention, the process for removing hydrogen sulfide from sour liquefied petroleum gas comprises:

(a) contacting the sour liquified petroleum gas in an extraction column with a liquid and regenerable absorbent to obtain a sweet liquefied petroleum gas which contains contaminants;

(b) supplying the sweet liquefied petroleum gas which contains contaminants to a membrane unit comprising a membrane selected from a permselective membrane and a porous hydrophobic membrane, a permeate outlet, and a retentate outlet; and (c) removing from the permeate outlet of the membrane unit a sweet liquified petroleum gas stream which is substantially free of contaminants and from the retentate outlet of the membrane unit a sweet liquified petroleum gas stream which contains concentrated contaminants.

Sour liquefied petroleum gas can include the lighter hydrocarbon components methane and ethane. These lighter components must be removed to obtain a marketable liquefied petroleum gas. As a result, the process of the present invention is modified to consist of a method for removing hydrogen sulfide from sour liquefied petroleum gas comprising:

(a) contacting the sour liquefied petroleum gas in an extraction column with a liquid and regenerable absorbent to obtain sweet liquefied petroleum gas which contains contaminants;

(b) splitting the sweet liquefied petroleum gas which contains contaminants into a liquid bottom stream and a gaseous overhead stream;

(c) supplying at least part of the liquid bottom stream to a membrane unit comprising a membrane selected from a permselective membrane and a porous hydrophobic membrane, a permeate outlet and a retentate outlet; and (d) removing from the permeate outlet of the membrane unit sweet liquefied petroleum gas which is substantially free of contaminants and from the retentate outlet of the membrane unit sweet liquefied petroleum gas which contains concentrated contaminants.

The sweet liquefied petroleum gas is split in a distillation column. In case the gaseous overhead contains entrained propane and/or butane, it is desirable to condense the gaseous overhead stream and to supply at least part of the condensed overhead stream to a membrane unit including a membrane selected from a permselective membrane and a porous hydrophobic membrane, a permeate outlet and a retentate outlet, and to remove from the permeate outlet of the membrane unit a treated liquefied overhead stream which is substantially free of contaminants and from the retentate outlet of the membrane unit a liquefied overhead stream which contains concentrated contaminants.

Sometimes it is required to produce a butane stream separated from a propane stream. Therefore an additional modification of the present invention comprises a method of removing hydrogen sulfide from sour liquefied petroleum gas comprising:

(a) contacting the sour liquefied petroleum gas in an extraction column with a liquid and regenerable absorbent to obtain sweet purified liquefied petroleum gas which contains contaminants;

(b) splitting the sweet liquefied petroleum gas which contains contaminants into a propane-rich overhead stream and a butane-rich bottom stream;

(c) supplying at least part of the propane-rich overhead stream to a first membrane unit comprising a membrane selected from a permselective membrane and a porous hydrophobic membrane, a permeate outlet and a retentate outlet;

(d) removing from the permeate outlet of the first membrane unit a treated propane-rich stream which is substantially free of contaminants and from the retentate outlet of the first membrane unit a propane-rich stream which contains concentrated contaminants;

(e) supplying at least part of the butane-rich bottom stream to a second membrane unit comprising a membrane selected from a permselective membrane and a porous hydrophobic membrane, a permeate outlet and a retentate outlet; and (f) removing from the permeate outlet of the second membrane unit a treated butane-rich stream which is substantially free of contaminants and from the retentate outlet of the second membrane unit a butane-rich stream which contains concentrated contaminants.

Either a permselective membrane or a porous hydrophobic membrane is included in the membrane unit.

The permselective membrane of the present invention is a membrane through which a fluid can permeate. The permeability (unit volume times unit length per unit area per unit time per unit pressure, dimension $M^{-1}L^3T$) of the membrane to a fluid is determined by the solubility of the fluid in the membrane and the diffusivity of the fluid through the membrane. Such a membrane is sometimes referred to as a dense membrane. The flux (unit volume per unit area per unit time, dimension $LT^{-1}$), of the fluid through the membrane is then the product of the permeability and the difference in partial pressure (unit mass times unit length per unit time per unit area, dimension $ML^{-1}T^{-2}$) of the fluid at either side of the membrane divided by the thickness of the membrane (unit length, dimension L).

A suitable permselective membrane is a porous substrate provided with a rubbery polymer such as a rubber or a hydrocarbon polymer above their glass-transition temperatures. Examples of suitable polymers include a silicone rubber such as polydimethylsiloxane, a fluorosilicone rubber, or a butadiene rubber. The rubbery polymer is supported on a porous substrate which is suitably polypropylene, polyvinylidene fluoride or tetrafluoroethylene.

The permselective membrane allows permeation of propane and butane while retaining absorbent, water and other contaminants.

A porous hydrophobic membrane is a porous membrane that retains water and consequently the membrane will retain the liquid and regenerable absorbent.

Suitable porous hydrophobic membranes include polypropylene, polytetrafluoroethylene, polyvinylidene difluoride and polyethylene with a pore size suitably from about 0.01 um to about 0.2 um.

The liquid and regenerable absorbent is an aqueous solution of an alkanol amine. Suitably the alkanol amine is di-isopropanol amine or diethanol amine.

DETAILED DESCRIPTION OF FIGURES

The method according to the present invention will now be explained by way of example in more detail with reference to the accompanying figures.

With reference to FIG. 1, sour liquefied petroleum gas is supplied through conduit 1 to an extraction column 2 in which the sour liquefied petroleum gas is contacted with liquid and regenerable absorbent in the form of an aqueous solution of di-isopropanol amine supplied to the extraction column 2 through conduit 3.

The extraction column 2 is provided with suitable contact means (not shown) to ensure transfer of hydrogen sulfide from the liquefied petroleum gas to the aqueous solution of di-isopropanol amine.

Sweet liquefied petroleum gas is removed from the extraction column 2 through conduit 5 and aqueous solution of di-isopropanol amine loaded with hydrogen sulfide is removed from the extraction column 2 through conduit 6. Loaded aqueous solution is supplied to a regeneration column (not shown) where hydrogen sulfide is removed from the aqueous solution to obtain a regenerated aqueous solution which is recycled to the extraction column through conduit 3.

The sweet liquefied petroleum gas contains contaminates, entrained absorbent and iron compounds, from the column and the conduits. To remove these contaminants, the sweet liquefied petroleum gas is supplied through conduit 5 to a membrane unit 10 including a permselective membrane 12, a permeate outlet and a retentate outlet. The permselective membrane comprises a rubbery polymer supported on a porous substrate. Part of the sweet liquefied petroleum gas permeates through the permselective membrane 12 and is removed from the permeate outlet through conduit 15 as sweet liquefied petroleum gas which is substantially free of contaminants. The contaminants do not permeate through the perm-selective membrane. They remain dissolved in the remainder of the sweet liquefied petroleum gas to form a sweet liquefied petroleum gas which contains concentrated contaminants and is removed from the retentate outlet of the membrane unit 10 through conduit 16.

Figure 2:
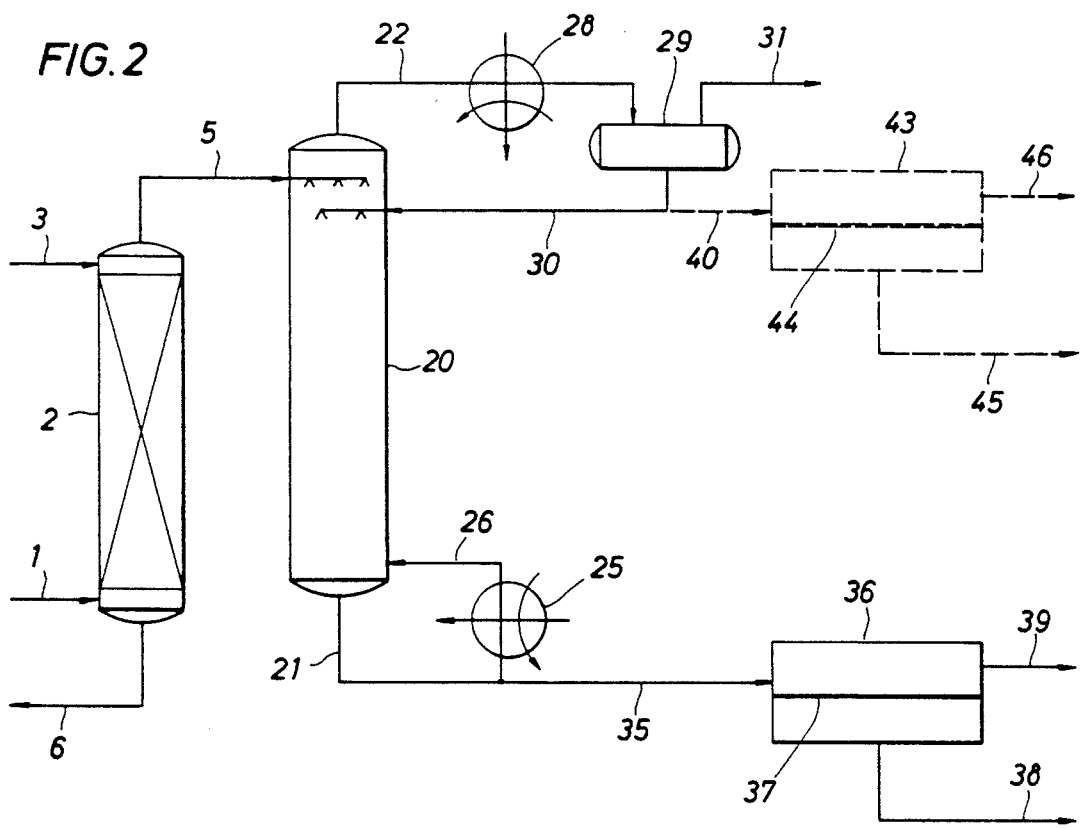
FIG. 2 is an alternative schematic drawing of equipment for carrying out the invention.

With reference to FIG. 2 [equipment having the same function as the equipment discussed with reference to FIG. 1 has been given the same reference number] sweet liquefied petroleum gas leaving the extraction column 2 through conduit 5 is supplied to a distillation column 20. Split liquefied petroleum gas is split in a liquid bottom stream removed from the distillation column 20 through conduit 21. The liquid bottom stream contains butane and propane. A gaseous overhead stream is removed from the column through conduit 22. The gaseous overhead stream contains methane and ethane and entrained butane and propane.

Part of the liquid bottom stream is vaporized in reboiler 25 and introduced as a stripping agent in the bottom of distillation column 20 through conduit 26. The gaseous overhead stream is condensed in cooler 28 and allowed to separate in vessel 29 into a liquid phase and a vapor phase, wherein the liquid phase is refluxed to the distillation column through conduit 30 and the vapor phase containing methane and ethane is removed through conduit 31.

The remaining part of the liquid bottom stream is supplied through conduit 35 to membrane unit 36 including a permselective membrane 37, a permeate outlet and a retentate outlet. From the permeate outlet of the membrane unit 36 is removed sweet liquefied petroleum gas which is substantially free of contaminants through conduit 38 and from the retentate outlet of the membrane unit 36 is removed contaminated sweet liquefied petroleum gas through conduit 39.

When it is not required to return all condensed overhead of the separation vessel 29 to the distillation column 20, part of the condensed overhead can be passed through conduit 40 (shown in dashed lines in FIG. 2) to a second membrane unit 43 which includes a permselective membrane 44, a permeate outlet and a retentate outlet. A treated liquefied overhead stream is removed from the permeate outlet of the membrane unit 43 through conduit 45 and a contaminated liquefied overhead stream is removed from the retentate outlet of the membrane unit 43 through conduit 46.

Figure 3:
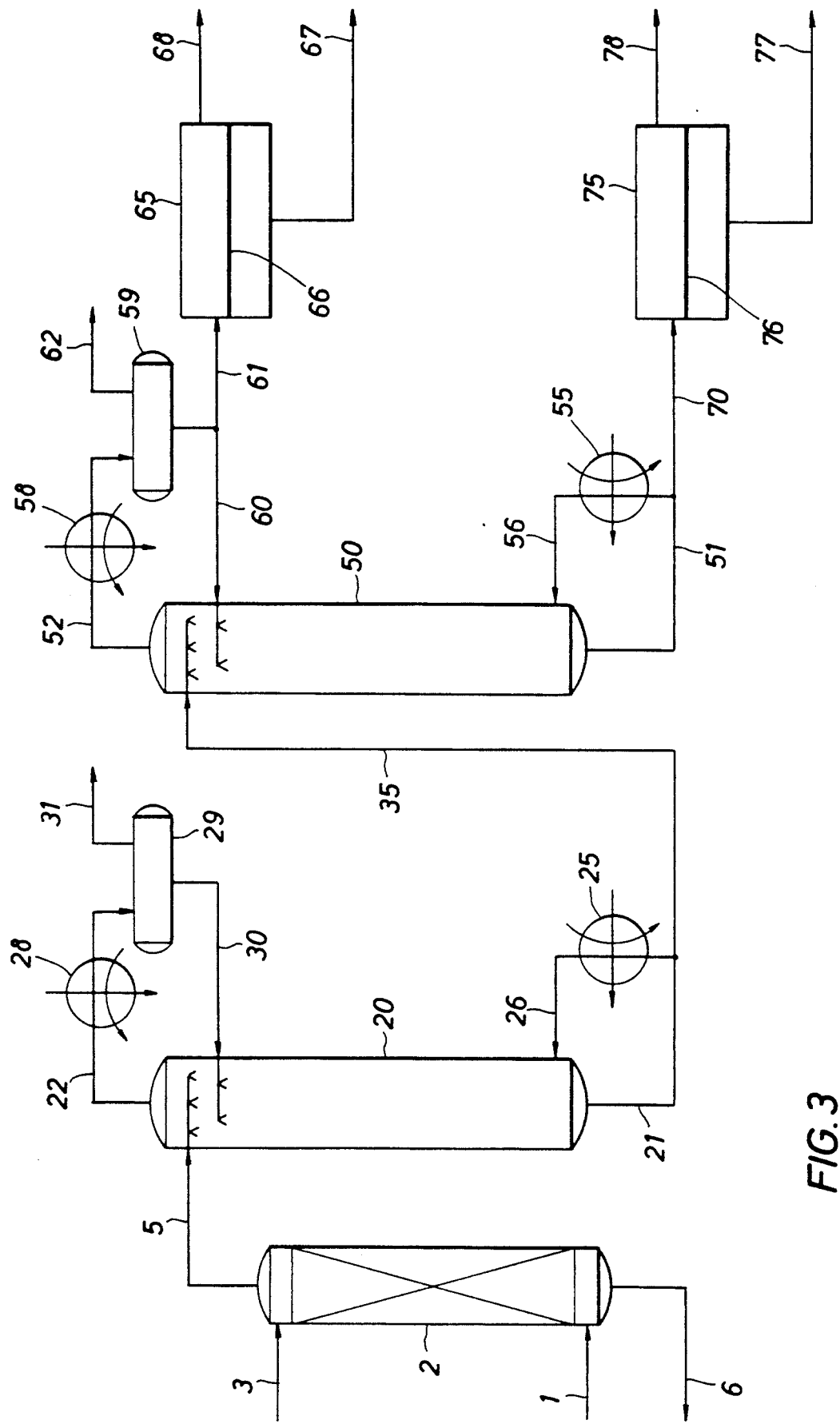
FIG. 3 is an additional alternative schematic drawing of equipment for carrying out the invention.

FIG. 3 exhibits equipment which can be used when it is required to produce a butane stream separated from a propane stream [equipment having the same function as the equipment discussed with reference to FIGS. 1 and 2 has been given the same reference numbers].

Instead of supplying the remaining part of the bottom stream through conduit 35 to a membrane unit, this stream is supplied to a second distillation column 50. The bottom stream is split into a liquid bottom stream containing butane which is removed from the distillation column 50 through conduit 51, and a gaseous overhead stream containing propane which is removed from the column 50 through conduit 52.

Part of the liquid bottom stream is vaporized in reboiler 55 and introduced as a stripping agent in the bottom of distillation column 50 through conduit 56. The gaseous overhead stream is condensed in cooler 58 and allowed to separate in vessel 59 in a liquid phase and a vapor phase, wherein part of the liquid phase is refluxed to the distillation column 50 through conduit 60 and the vapor phase is removed through conduit 62.

The remaining part of the propane-rich overhead stream is supplied through conduit 61 to a first membrane unit 65 including a permselective membrane 66, a permeate outlet and a retentate outlet. From the permeate outlet of the first membrane unit 65, a treated propane-rich stream is removed through conduit 67, and from the retentate outlet of the first membrane unit 65, a contaminated propane-rich stream is removed through conduit 68. The remaining part of the butane-rich bottom stream is supplied through conduit 70 to a second membrane unit 75 including a permselective membrane 76, a permeate outlet and a retentate outlet. From the permeate outlet of the second membrane unit 75, a treated butane-rich stream is removed through conduit 77, and from the retentate outlet of the second membrane unit 75 a contaminated butane-rich stream is removed through conduit 78.

In the method according to the present invention as described with reference to FIGS. 1–3, each membrane unit includes a permselective membrane. The operation of the membrane units does not change when the permselective membrane is replaced by a porous hydrophobic membrane.

Distillation column 20 is sometimes referred to as a deethanizer and distillation column 50 is sometimes referred to as a depropanizer, the pressure in the deethanizer is suitably from about 15 bar to about 20 bar and the pressure in the depropanizer is suitably from about 12 bar to about 16 bar. Additional details regarding these particular columns is found, for example, in The Petroleum Handbook, sixth edition, 1983, pages 255 and 256.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

What is claimed is:

1. A method of removing hydrogen sulfide from sour liquefied petroleum gas comprising:
   (a) contacting the sour liquefied petroleum gas in an extraction column with a liquid and regenerable absorbent to obtain a sweet liquefied petroleum gas which contains contaminants;
   (b) supplying the sweet liquefied petroleum gas which contains contaminants to a membrane unit comprising a membrane selected from a permselective membrane and a porous hydrophobic membrane, a permeate outlet and a retentate outlet; and
   (c) removing from the permeate outlet of the membrane unit sweet liquefied petroleum gas which is substantially free of contaminants and from the retentate outlet of the membrane unit sweet liquefied petroleum gas in which the contaminants are concentrated.

2. The method of claim 1 wherein the membrane is a permselective membrane.

3. The method of claim 2 wherein the permselective membrane comprises a porous substrate provided with a rubbery polymer.

4. The method of claim 3 wherein the porous substrate is polypropylene, polyvinylidene fluoride or tetrafluoroethylene.

5. The method of claim 4 wherein the polymer is polydimethylsiloxane, a fluorosilicone rubber or a butadiene rubber.

6. The method of claim 1 wherein the membrane is a porous hydrophobic membrane.

7. The method of claim 6 wherein the porous hydrophobic membrane is polypropylene, polytetrafluoroethylene, polyvinylidene difluoride or polyethylene.

8. The method of claim 6 wherein the pore size of the porous hydrophobic membrane is from about 0.01 um to about 0.2 um.

9. A method of removing hydrogen sulfide from sour liquefied petroleum gas comprising:

(a) contacting the sour liquefied petroleum gas in an extraction column with a liquid and regenerable absorbent to obtain sweet liquefied petroleum gas which contains contaminants;

(b) splitting the sweet liquefied petroleum gas which contains contaminants into a liquid bottom stream and a gaseous overhead stream;

(c) supplying at least part of the liquid bottom stream to a first membrane unit comprising a membrane selected from a permselective membrane and a porous hydrophobic membrane, a permeate outlet and a retentate outlet; and (d) removing from the permeate outlet of the membrane unit sweet liquefied petroleum gas which is substantially free of contaminants and from the retentate outlet of the membrane unit sweet liquefied petroleum gas in which the contaminants are concentrated.

10. The method of claim 9 which further comprises condensing the gaseous overhead stream and supplying at least part of the condensed overhead stream to a second membrane unit comprising a membrane selected from a permselective membrane and a porous hydrophobic membrane, a permeate outlet and a retentate outlet, and removing from the permeate outlet of the membrane unit a treated liquefied overhead stream and from the retentate outlet of the membrane unit a contaminated liquefied overhead stream.

11. The method of claim 10 wherein the membrane of the first membrane unit and the second membrane is a permselective membrane.

12. The method of claim 11 wherein the permselective membrane comprises a porous substrate provided with a rubbery polymer.

13. The method of claim 12 wherein the porous substrate is polypropylene, polyvinylidene fluoride or tetrafluoroethylene.

14. The method of claim 13 wherein the polymer is polydimethylsiloxane, a fluorosilicone rubber or a butadiene rubber.

15. The method of claim 9 wherein the membrane of the first membrane unit and the second membrane is a porous hydrophobic membrane.

16. The method of claim 15 wherein the porous hydrophobic membrane is polypropylene, polytetrafluoroethylene, polyvinylidene difluoride or polyethylene.

17. The method of claim 15 wherein the pore size of the porous hydrophobic membrane is from about 0.01 um to about 0.2 um.

18. A method of removing hydrogen sulfide from sour liquefied petroleum gas comprising:

(a) contacting the sour liquefied petroleum gas in an extraction column with a liquid and regenerable absorbent to obtain sweet liquefied petroleum gas which contains contaminants;

(b) splitting the sweet liquefied petroleum gas which contains contaminants into a propane-rich overhead stream and a butane-rich bottom stream;

(c) supplying at least part of the propane-rich overhead stream to a first membrane unit comprising a membrane selected from a permselective membrane and a porous hydrophobic membrane, a permeate outlet and a retentate outlet;

(d) removing from the permeate outlet of the first membrane unit a treated propane-rich stream and from the retentate outlet of the first membrane unit a contaminated propane-rich stream;

(e) supplying at least part of the butane-rich bottom stream to a second membrane unit comprising a membrane selected from a permselective membrane and a porous hydrophobic membrane, a permeate outlet and a retentate outlet; and (f) removing from the permeate outlet of the second membrane unit a treated butane-rich stream and from the retentate outlet of the second membrane unit a contaminated butane-rich stream.

19. The method of claim 18 wherein the membrane of the first membrane unit and the second membrane unit is a permselective membrane. permselective membrane.

20. The method of claim 19 wherein the permselective membrane comprises a porous substrate provided with a rubbery polymer.

21. The method of claim 20 wherein the porous substrate is polypropylene, polyvinylidene fluoride or tetrafluoroethylene.

22. The method of claim 21 wherein the polymer is polydimethylsiloxane, a fluorosilicone rubber or a butadiene rubber.

23. The method of claim 18 wherein the membrane of the first membrane unit and the second membrane unit is a porous hydrophobic membrane.

24. The method of claim 23 wherein the porous hydrophobic membrane is polypropylene, polytetrafluoroethylene, polyvinylidene difluoride or polyethylene.

25. The method of claim 23 wherein the pore size of the porous hydrophobic membrane is from about 0.01 um to about 0.2 um.

* * * * *